United States Patent [19]

Segal et al.

[11] Patent Number: 4,678,772

[45] Date of Patent: Jul. 7, 1987

[54] COMPOSITIONS CONTAINING GLYCYRRHIZIN

[75] Inventors: Ruth Segal; Sara Pisanty; Emma Azaz, all of Jerusalem, Israel

[73] Assignee: Yissum Research Development Company of the Hebrew University of Jerusalem, Jerusalem, Israel

[21] Appl. No.: 654,148

[22] Filed: Sep. 25, 1984

Related U.S. Application Data

[63] Continuation-in-part of Ser. No. 470,293, Feb. 28, 1983, abandoned.

[51] Int. Cl.$^4$ ............................................. A61K 31/70
[52] U.S. Cl. .................................................... 514/25
[58] Field of Search .......................................... 514/25

[56] References Cited

PUBLICATIONS

Chemical Abstracts 92:104967m (1980).
Chemical Abstracts 92:122494j (1980).
Bauer et al., Chemotherapy of Virus Diseases, vol. 1, Pergamon Press, N.Y., N.Y., 1973, pp. 250-253 and 319-321.

*Primary Examiner*—Jerome D. Goldberg
*Attorney, Agent, or Firm*—Browdy and Neimark

[57] ABSTRACT

There are provided compositions for the prevention and for the treatment of oral diseases based on glycyrrhizin, and a drug, and for the treatment of oral, nasal and genital lesions due to Herpes simplex, based on glycyrrhizin in combination with an antiviral agent such as idoxuridine.

2 Claims, No Drawings

COMPOSITIONS CONTAINING GLYCYRRHIZIN

RELATION TO OTHER APPLICATIONS

The present patent application is a continuation-in-part of patent application Ser. No. 470,293, filed Feb. 28, 1983, now abandoned.

FIELD OF THE INVENTION

There are provided preparations having a synergistic effect, which comprise glycyrrhizin in an aqueous medium in combination with an effective drug. These are of value in the treatment of various oral diseases and especially for aphthous stomatitis. They are of value for the treatment of lesions caused by herpes simplex. The drug of choice for the treatment of stomatitis is triamcinolone, and for the treatment of Herpex simplex the drug of choice is idoxuridine (IDU).

SUMMARY OF THE INVENTION

According to the present invention there are provided novel compositions of matter for the treatment of oral diseases and for the treatment of labial, nasal and genital lesions caused by herpes simplex. The novel pharmaceutical compositions comprise an active ingredient or a combination of some active ingredients in an aqueous carrier containing glycyrrhizin. Glycyrrhizin is the glucuronide of glycyrrhetic acid and is a constituent of licorice. The syrup of glycyrrhiza has been used as a demulcent, an expectorant and a pharmaceutical vehicle. It has now been discovered that at certain concentrations glycyrrhizin possesses excellent dispersing properties and that it forms stable gels which can be used advantageously in oral medicine. The novel preparations have excellent rheological properties for oral application. The substance has a sweet taste, yet tests carried out have shown that glycyrrhizin, in the concentrations tested, inhibits the adherence of *Streptococcus mutans;* and of *Actinomyces viscusus,* which are amongst the main cariogenic microorganisms, to teeth.

BACKGROUND OF THE INVENTION

Among the common primary diseases occurring in the oral cavity are allergic stomatitis, oral candidiasis, herpetic stomatitis, aphthous ulcerations, etc.

In diseases such as leukemias, pemphigus vulgaris, erythema multiforme, etc., there are secondary signs which manifest themselves in inflammatory and ulcerative forms in the mouth.

These local conditions cause not only serious discomfort to the patient but are a source of infection to the whole body. Medication is often administered systemically, thus exposing the patient to various side-effects. Undoubtedly, the local application of a drug is preferable, whenever possible.

The efficiency of local applications depends, among other factors, on the effectiveness of the contact to the mucosa and its duration. It is customary, therefore, to use a vehicle that facilitates the application and prolongs the contact with the affected site.

Special problems are encountered in oral medications. The mouth is rich with flora, and having a constant temperature of 36.8° and a high humidity, it provides an ideal medium for the development of microorganisms.

An efficient vehicle for oral treatment must withstand the constant saliva rinsing, and must resist enzymatic decomposition. Furthermore, the vehicle must have an agreeable taste and, smell, and obviously, must be non-toxic. The medicine must be applied in water-soluble vehicle since an oily base will prevent the direct contact of the drug with the affected area.

According to the present invention, there are also provided compositions for the treatment of lesions (oral, nasal and genital) caused by herpes simplex.

STATE OF THE PRIOR ART

The existing preparations for treating diseases of the oral cavity are either inpalatable, or are intended for dermal application. For example, antiinflammatory ointments are prepared in oily bases, thus, being non-effective for oral use. Syrups which are often used for topical oral application in order to disguise the taste of drugs, stimulate the formation of dental caries.

In the course of the preparation of galenic emulsions and suspensions, we realized that there exists a natural product, glycyrrhizin, which possesses excellent dispersing qualities.

At concentrations ranging between 1-2%, glycyrrhizin forms stable gels with ideal rheological properties for pharmaceutical preparations. Furthermore, glycyrrhizin is well known for its agreeable sweet taste, which has caused it to be a valuable additive in the food industry.

These qualities make the glycyrrhizin gel a highly appropriate vehicle for medications to be topically applied to the oral cavity and to all other mucous membranes.

Pompei et al. presented results relating to the effect of glycyrrhizin as inhibitor of viruses (see *Nature* 1979, 281(5733). 688–690; *Riv. Farmacol. Ter.* 1979, 10 (3) 281–4). However, these results were confined to cell cultures and no data are presented with regard to the in vivo effects of glycyrrhizin on herpes simplex. Experiments have been carried out by us indicating that glycyrrhizin when applied in vivo, lacks any substantial effect on herpes simplex infections.

Idoxuridine (IDU) is a well known antiviral agent and has proved effective in the treatment of lesions of herpes (see for example Bauer et al., Chemotherapy of Virus diseases, Pergamon Press, 1973, 50–53).

The present invention is a composition of IDU in glycyrrhizin-gel. It has the following considerable advantages over the conventional IDU ointment: On application an immediate relief in the pain is obtained; healing is speeded up considerably; the aqueous base is absorbed very quickly and therefore the unaesthetic effect of the ointment base preparations is eliminated; an 0.2% concentration of the present invention achieves better results than 0.5% concentrations IDU in the conventional ointment. Results and comparative studies are provided in the experimental section.

Infections caused by herpes simplex affect mucous membranes of the mouth, nose and genitalia. According to the present invention there are provided compositions which are effective for the treatment of herpes nasalis and labialis. This composition is advantageously provided in the form of an ointment or as a lotion. The efficacy of the novel preparations was compared with compositions based on the use of idoxuridine (IDU) as active ingredient, which is widely used for the treatment of such afflictions.

When the novel compositions of the present invention are applied (advantageously as a gel), pain disappears almost immediately and the time of healing is drastically reduced. When the medication is used in prodromic stages, the lesions are abortive.

Pharmaceutical compositions based on idoxuridine (IDU have been in use for more than 10 years. In view of the extensive experience with such preparations, and in view of the comparison with the preparations of the present invention, a synergistic effect between the antiviral compound IDU and the antiinflammatory component glycyrrhizin has been established.

The novel pharmaceutical compositions of the present invention comprise a quantity of from about 0.5 to 2.5% glycyrrhizin, and preferably from 1 to 2 percent of this substance, in an aqueous medium, in combination with active ingredients such as antibiotics, fungicides, antiinflammatory steroids, and the like.

According to the present invention, there are also provided compositions for the treatment of oral, nasal and genital lesions caused by herpes simplex. These contain an effective antiviral agent such as idoxuridine (IDU), in combination with glycyrrhrizin. The novel compositions are highly effective and it is believed that this is due to a synergistic effect of these two constituents.

As glycyrrhizin is accepted in the food industry and also as an adjuvant in pharmaceuticals for disguising unpleasant flavors, no toxicological problems arise as to the use of this natural substance as an ingredient of the novel compositions of the present invention.

The following examples, which are to be construed in a non-limitative manner, illustrate the present invention. Unless otherwise defined, the following examples refer to aqueous solutions. Percents are by weight.

EXAMPLE 1

Oral Antimycotic Preparation for Treatment of Oral Candidiasis

An oral pharmaceutical preparation in gel form was prepared as follows:
Nystatin: 2%
Glycyrrhizin: 1%
Methyl Cellulose-4000: 2%
Propyl gallate: 0.1%
Methyl paraben: 0.15%
1% Vanillin alcoholic solution: 0.5%
in phosphate buffer pH 7.0

EXAMPLE 2

Antibiotic Gel for Treating Oral Infections (Diseases)

0.5% Neomycin
1% Bacitracin
1.25% Glycyrrhizin
in water

EXAMPLE 3

Antiinflammatory Preparation for Treatment of Oral Ulcerations:

Triamcinolone: 0.1%
Glycyrrhizin: 1%
Benzoic acid: 0.1%
in water

EXAMPLE 4

Preparation for Treatment Aphthous Mucosa:

Estradiol: 0.1–0.01%
Glycyrrhizin: 2%
Benzoic acid: 0.1%
in water

EXAMPLE 5

Mestranol: 0.001%
Glycyrrhizin: 2%
Benzoic acid: 0.1%
in water

EXAMPLE 6

Premarin: 0.063%
Glycyrrhizin: 2%
Benzoic acid: 1%
in water

EXAMPLE 7

Anticariogenic Gels and Mouth Washes (a)

NaF: 0.2%
Glycyrrhizin: 1.25%
in $H_3PO_4$—: 0.1M (b)

NaF: 2%
Glycyrrhizin: 1.25%
in $H_3PO_4$: 0.1M (c)

NaF: 0.01%
Glycyrrhizin: 0.25%
in water.

Preparations for the Treatment of Mucosal Lesions, oral, nasal and genital, caused by Herpes simplex Virus

EXAMPLE 8

Idoxuridine (IDU): 0.2%
Glycyrrhizin: 2.0%
Benzoic acid: 0.1%
in water

EXAMPLE 9

Idoxuridine (IDU): 0.2%
Glycyrrhizin: 1.5%
Benzoic acid: 0.1%
in water

EXAMPLE 10

Idoxuridine: 0.1%
Glycyrrhizin: 2%
Benzoic acid: 0.1%
in water

EXAMPLE 11

IDU: 0.1%
Glycyrrhizin: 1.5%
Benzoic acid: 0.1%
in water

EXAMPLE 12

Treatment of Herpes Simplex

A study was carried out to evaluate the effectivity of the mode of action of IDU in an aqueous glycyrrhizin base, and to compare it with conventional preparations such as VIRUSAN ointment produced by Ikapharm, Israel, which contains the active IDU in an ointment base at a concentration of 0.5%.

The comparison was made with preparations according to Example 8 of the present application. This was prepared by dissolving 0.2 g IDU and 2.0 g glycyrrhizin in 100 ml of a 0.1% solution of benzoic acid in water at elevated temperature with stirring. After about 5 minutes a homogeneous mixture was obtained, and after cooling there was obtained a transparent gel.

The study group encompassed 120 patients who had been referred to the Oral Medical Clinic of Hadassa University Hospital in Jerusalem by their physicians. The patients ranged from 18 to 60 years; there were 82 females and 38 males. These were divided into 3 groups; the objects and details of the investigation were explained and the consent of the participants was obtained. The tests were carried out by the double-blind method. The first group was treated with a gel of the vehicle (glycyrrhizin) alone. The second group was treated with a preparation according to the above (Example 8). The third group was treated with VIRUSAN produced by Ikapharm, which contains 0.5% IDU in an ointment base.

The patients applied the preparation every 2 hours during day time until crusting was achieved. The patients recorded the duration of the lesions and the degree of pain.

The results indicate that:
a. The vehicle by itself gave immediate relief of pain after application. The time of healing, which was about 8 to 14 days without any treatment, was reduced to about 8 to 10 days, which is not a significant result.
b. The VIRUSAN ointment did not relieve pain but resulted in a reduction of healing time to about 4 to 8 days.
c. The preparation of Example 8 relieved pain immediately and shortened the time of healing to 2-6 days (in very severe cases); when used in the prodromic stage, the lesions were abortive; the appearance of the ointment was much superior to that of VIRUSAN. The acceptance of the novel preparation was favorable because of its smooth consistency and transparent appearance.

If healing takes place without treatment, severe ulcerations may result. The preparations according to the present invention reduce pain very markedly, the area of ulceration is substantially reduced and healing time is shortened. One of the patients had been treated before with interferon, and indicated that the composition of the present invention gave a better effect.

EXAMPLE 13

Treatment of Aphthous Stomatitis

A composition according to Example 3 was used. This was prepared from 32 ml distilled water, 50 ml of 0.2% benzoic acid in water, and 2 g glycyrrhizin, which were warmed with stirring until a clear solution was obtained, after which 18 ml ethanol were added. While still warm the mixture was poured into a mortar containing a mixture of 100 mg triamcinolone acetonide and a few drops of glycerin. Thorough mixing resulted in a homogeneous suspension which gelatinized upon cooling.

Experiments were carried out with compositions of the invention for the treatment of recurrent aphthous stomatitis. The composition used was according to Example 3. The study was carried out with 134 patients ranging from 7 to 62 years, mean age 31-25 years, with 56 females and 78 males. Major aphthosis was found in 57 patients and minor aphthosis in 77. The objects of the study were explained to the patients and their consent was obtained. The patients kept full daily ulcer records and visited the clinic weekly for at least 6 months; recurrent aphthous stomatitis (RAS) was present for at least one year. The patients recorded localization, number, size and duration of ulcers and degree of pain on daily record charts. The study was by the double blind method. The patients were divided into 3 groups, the first received glycyrrhizin alone (49 cases), the second received the vehicle plus triamcinolone, 0.1% (65 cases), and the third received Kenalog in Orabase (Squibb) (20 cases).

The patients applied the drug topically three times a day, continuing administration until the ulcer had healed. They were requested to abstain from eating and drinking for 30 minutes following each application.

The following results were obtained:
(1) Patients treated with glycyrrhizin alone:
major aphthosis: improvement 22.7%; no change: 77.3%.
minor aphthosis: improvement 68%; no change: 26%; remission: 1 case.
(2) Patients treated with triomcinolone 0.1% in glycyrrhizin:
major aphthosis: improvement 60%: no change 40%.
minor aphthosis: improvement 46%; remission 46%.
(3) Patients treated with Kenalog in Orabase showed similar results as those of group (2). The Kenalog preparation caused a certain discomfort during its use and a number of patients discontinued its use due to this. The preparation according to the present invention is much superior in this respect.

It is apparent that the good therapeutic effect is due to a synergistic effect between glycyrrhizin and triamcinolone. Due to its palatable taste and smooth consistency, the novel composition is more readily accepted by the patients than the conventional preparations.

We claim:
1. A preparation for the treatment of herpes simplex lesions comprising about 0.2% by weight of idoxuridine in about 2.0% by weight of glycyrrhizin.
2. A method for the treatment of lesions caused by herpes simplex comprising topically administering to the affected areas in the oral cavity of a patient having lesions caused by herpes simplex about 0.2% by weight of idoxuridine in about 2.0% by weight of glycyrrhizin.

* * * * *